(12) United States Patent
Hughes et al.

(10) Patent No.: US 12,727,907 B2
(45) Date of Patent: Sep. 8, 2026

(54) TISSUE-REMOVING CATHETER WITH ADAPTIVE TORQUE CONTROL

(71) Applicant: Medtronic Vascular, Inc., Santa Rosa, CA (US)

(72) Inventors: Luke Hughes, Galway (IE); Aram Jamous, Athenry (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 2 days.

(21) Appl. No.: 18/730,939

(22) PCT Filed: Jan. 13, 2023

(86) PCT No.: PCT/IB2023/050319
§ 371 (c)(1),
(2) Date: Jul. 22, 2024

(87) PCT Pub. No.: WO2023/139457
PCT Pub. Date: Jul. 27, 2023

(65) Prior Publication Data

US 2025/0099130 A1 Mar. 27, 2025

Related U.S. Application Data

(60) Provisional application No. 63/301,308, filed on Jan. 20, 2022.

(51) Int. Cl.
*A61B 17/3207* (2006.01)
*A61B 17/00* (2006.01)
(Continued)

(52) U.S. Cl.
CPC ................. *A61B 17/320758* (2013.01); *A61B 2017/00039* (2013.01); *A61B 2017/00398* (2013.01);
(Continued)

(58) Field of Classification Search
CPC ...... A61B 17/320758; A61B 2090/064; A61B 2090/066; A61B 2017/00039;
(Continued)

(56) References Cited

U.S. PATENT DOCUMENTS 4,926,858 A 5/1990 Gifford, III et al.
5,602,449 A * 2/1997 Krause ................ G05B 19/232 318/400.11
(Continued)

FOREIGN PATENT DOCUMENTS

WO WO2010056714 A1 5/2010

OTHER PUBLICATIONS

International Search Report for PCT/IB2023/050319, Mar. 23, 2023, 14 pages, Rijswijk, Netherlands.

*Primary Examiner* — Shaun L David
*Assistant Examiner* — Cherie M Poland
(74) *Attorney, Agent, or Firm* — Stinson LLP

(57) ABSTRACT

A tissue-removing catheter includes a torque sensor that senses torque from a motor acting on a component of the catheter. A linear force sensor senses a linear force from the advancer acting on a component of the catheter. A controller is in operative communication with the motor, the torque sensor, and the linear force sensor. The controller controls a speed of the motor based on the sensed torque and the sensed linear force during operation of the tissue-removing catheter. The linear force sensor may sense linear force imparted on a liner of the catheter.

18 Claims, 21 Drawing Sheets

(51) Int. Cl.
*A61B 17/32* (2006.01)
*A61B 90/00* (2016.01)

(52) U.S. Cl.
CPC ............. *A61B 2017/320004* (2013.01); *A61B 2090/064* (2016.02); *A61B 2090/066* (2016.02)

(58) Field of Classification Search
CPC ......... A61B 2017/00398; A61B 2017/320004; A61B 17/32075; A61B 2017/00017
See application file for complete search history.

(56) References Cited

U.S. PATENT DOCUMENTS

| | | | | |
|---|---|---|---|---|
| 6,102,926 | A | 8/2000 | Tartaglia et al. | |
| 10,226,276 | B2 | 3/2019 | Kessler | |
| 10,368,902 | B2 | 8/2019 | Kessler et al. | |
| 11,426,193 | B2 | 8/2022 | Kessler | |
| 11,931,063 | B2 | 3/2024 | Hansen | |
| 12,220,145 | B2 | 2/2025 | Jamous et al. | |
| 2016/0354108 | A1* | 12/2016 | Nakano | A61B 17/320758 |
| 2018/0317952 | A1* | 11/2018 | Jamous | A61B 17/320758 |
| 2019/0175211 | A1* | 6/2019 | Carlson | A61B 17/32002 |
| 2020/0289148 | A1* | 9/2020 | Masubuchi | A61B 17/320725 |
| 2021/0298751 | A1* | 9/2021 | Hart | A61B 17/07207 |
| 2025/0072929 | A1 | 3/2025 | Jamous et al. | |
| 2025/0099130 | A1 | 3/2025 | Hughes et al. | |

* cited by examiner

TISSUE-REMOVING CATHETER WITH ADAPTIVE TORQUE CONTROL

STATEMENT OF RELATED CASES

This application is a 371 of International or Continuation Application No. PCT/IB2023/050319, filed Jan. 13, 2023, which claims the benefit of U.S. Provisional Application No. 63/301,308, filed Jan. 20, 2022, the entire contents of which are incorporated herein by reference.

FIELD

The present disclosure generally relates to a tissue-removing catheter, and more particular, to a tissue-removing catheter including an adaptive torque control.

BACKGROUND

Tissue-removing catheters such as atherectomy catheters are used to remove tissue from a blood vessel to open the blood vessel and improve blood flow through the vessel. Atherectomy catheters typically abrade, cut, excise, ablate or otherwise remove the unwanted tissue.

SUMMARY

In one aspect, the present disclosure is directed to a tissue-removing catheter for removing tissue in a body lumen. The tissue-removing catheter comprises an elongate body having an axis and proximal and distal end portions spaced apart from one another along the axis. The elongate body is sized and shaped to be received in the body lumen. A motor is operatively coupled to the elongate body for imparting torque to the elongate body to drive rotation of the elongate body. A tissue-removing element is mounted on the distal end portion of the elongate body and configured to rotate with the elongate body. The tissue-removing element is configured to remove the tissue as the tissue-removing element is rotated by the elongate body within the body lumen. An advancer is operatively coupled to the motor to selectively apply a linear force to the motor together with the elongate body and the tissue-removing element to linearly advance and retract the motor, the elongate body and the tissue-removing element. A torque sensor is configured to sense torque from the motor acting on a component of the catheter. A linear force sensor is configured to sense a linear force from the advancer acting on a component of the catheter. A controller is in operative communication with the motor, the torque sensor, and the linear force sensor. The controller is configured to control a speed of the motor based on the sensed torque and the sensed linear force during operation of the tissue-removing catheter.

In another aspect, the disclosure is directed to a drive shaft having an axis and proximal and distal end portions spaced apart from one another along the axis. The drive shaft is sized and shaped to be received in the body lumen. A liner is received in the elongate drive shaft. The liner is configured to receive a guidewire therein. A motor is operatively coupled to the drive shaft for imparting torque to the drive shaft to drive rotation of the drive shaft. A tissue-removing element is mounted on the distal end portion of the drive shaft and configured to rotate with the drive shaft. The tissue-removing element is configured to remove the tissue as the tissue-removing element is rotated by the drive shaft within the body lumen. An advancer is operatively coupled to the motor to selectively apply a linear force to the motor together with the drive shaft and the liner to linearly advance and retract the drive shaft, the liner, and the tissue-removing element. A linear force sensor is configured to sense a linear force indicative of linear force that is imparted by the advancer. The linear force sensed by the linear force sensor is a linear force imparted on the liner.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Corresponding reference characters indicate corresponding parts throughout the drawings.

DETAILED DESCRIPTION

The present disclosure is generally directed to a tissue-removing catheter for removing tissue in a body lumen. In one embodiment, the catheter is an atherectomy device (e.g., rotational atherectomy device) suitable for removing (e.g., abrading, debulking, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a vessel wall (e.g., coronary arterial wall, etc.). The catheter may be used to facilitate percutaneous coronary angioplasty (PTCA) or the subsequent delivery of a stent. Features of the disclosed embodiments may also be suitable for treating chronic total occlusion (CTO) of blood vessels and stenosis of other body lumens and other hyperplastic and neoplastic conditions in other body lumens, such as the ureter, the biliary duct, respiratory passages, the pancreatic duct, the lymphatic duct and the like. Neoplastic cell growth will often occur as a result of a tumor surrounding and intruding into a body lumen. Removal of such material can thus be beneficial to maintain patency of the body lumen. In general, embodiments of the tissue-removing catheter described herein relate to an adaptive torque control for controlling voltage (e.g., speed) versus current (e.g., torque) of the catheter.

Example of a Suitable Tissue-Removing Catheter

The following is a description of a suitable tissue-removing catheter in which embodiments of the present invention may be incorporated. It is understood that this description of a suitable tissue-removing catheter is non-limiting, and a suitable tissue-removing catheter may omit certain component and/or include additional component(s).

Figure 1:
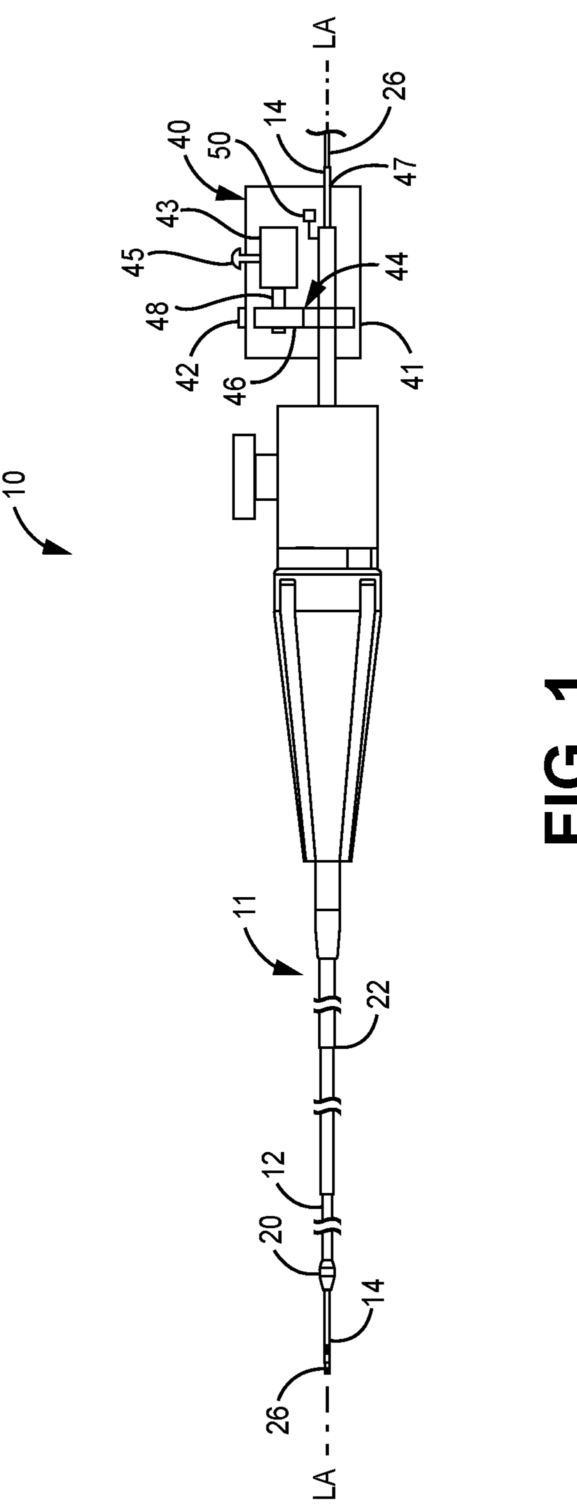
FIG. 1 is a schematic illustration of a catheter of the present disclosure.
Figure 2:
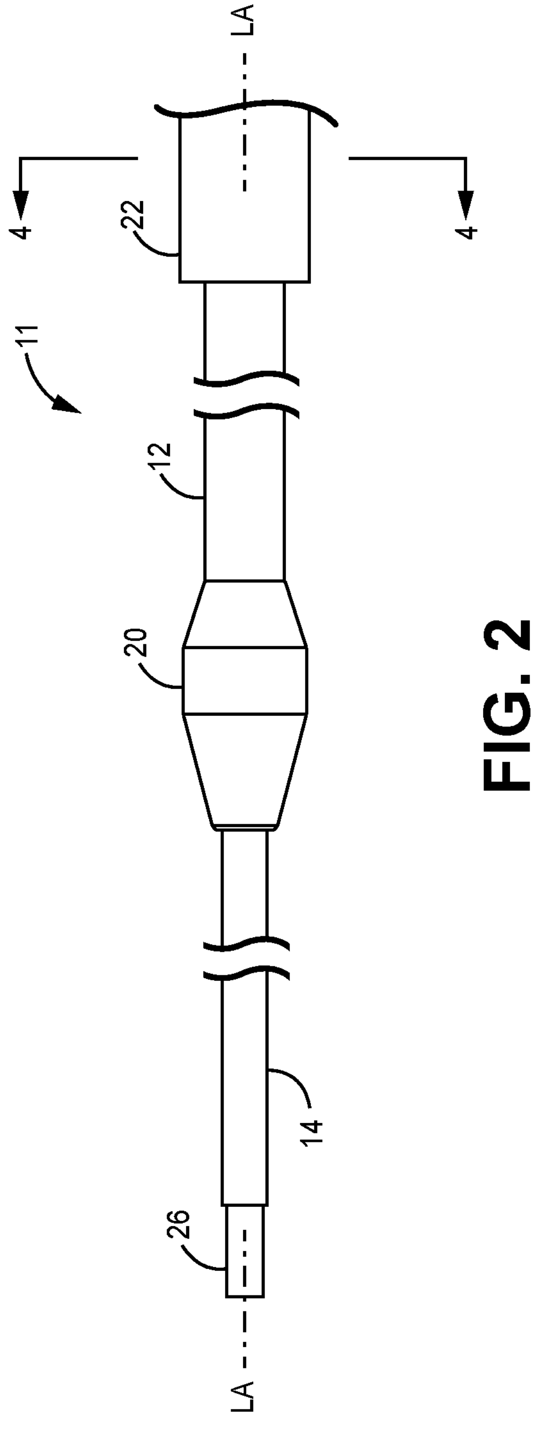
FIG. 2 is an enlarged elevation of a distal end portion of the catheter.
Figure 3:
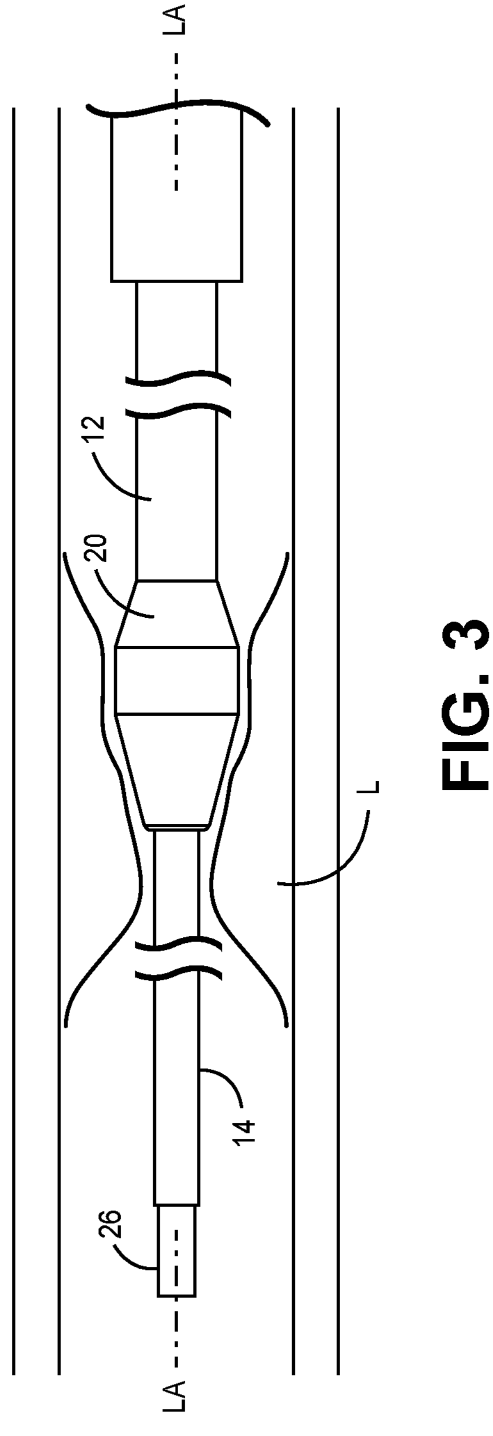
FIG. 3 is the enlarged elevation of a distal end portion of the catheter abrading though a lesion.

Referring to FIGS. 1-3, an exemplary embodiment of a rotational tissue-removing catheter for removing tissue (e.g., a lesion L) in a body lumen is generally indicated at reference number 10. The illustrated catheter 10 includes an elongate catheter body, generally indicated at reference numeral 11, having proximal and distal end portions. In one example, the catheter body 11 is sized for being received in a blood vessel of a subject. Thus, the catheter body 11 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

As shown in FIGS. 1-3, the catheter body 11 comprises an elongate body 11 e.g., a drive shaft such as drive coil 12, disposed around an elongate inner liner 14. The drive coil 12 and inner liner 14 extend along a longitudinal axis LA of the catheter body 11 from a proximal end portion to a distal end portion of the catheter body. An abrasive burr 20 (or other tissue-removing element) is disposed on a distal end of the drive coil 12 and is configured for rotation to remove the lesion L from a body lumen. The abrasive burr 20 may have an abrasive outer surface formed, for example, by a diamond grit coating, surface etching, or the like.

Figure 4:
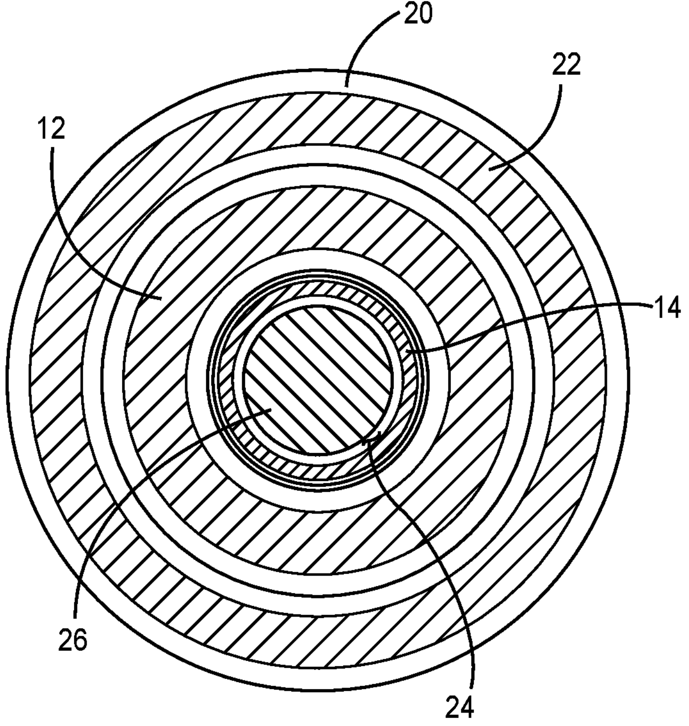
FIG. 4 is a cross section taken through line 4-4 in FIG. 2.

As shown in FIG. 4, an isolation sheath 22 is disposed through the burr 20 and around the drive coil 12. The drive coil 12 and the inner liner 14 are both configured to translate relative to the isolation sheath 22. The isolation sheath 22 isolates the body lumen from at least a portion of the drive coil 12 and inner liner 14. The space between the isolation sheath 22 and the drive coil 12 allows for the drive coil to rotate within the sheath and provides an area for saline perfusion between the sheath and drive coil. The inner liner 14 defines a guidewire lumen 24 for slidably receiving a guidewire 26 therein so that the catheter 10 can be advanced through the body lumen by traveling along the guidewire. The guidewire can be a standard 0.014-inch outer diameter, 300 cm length guidewire. In certain embodiments, the inner liner 14 may have a lubricious inner surface for sliding over the guidewire 26 (e.g., a lubricious surface may be provided by a lubricious polymer layer or a lubricious coating). In the illustrated embodiment, the guidewire lumen 24 extends all the way through the length of the inner liner 14 such that the guidewire 26 is extendable along an entire working length of the catheter 10. In one embodiment, the overall working length of the catheter 10 may be between about 135 cm (53 inches) and about 142 cm (56 inches). In use, the guidewire 26 may extend about 40 mm (1.6 inches) past a distal end of the inner liner 14.

Figure 5:
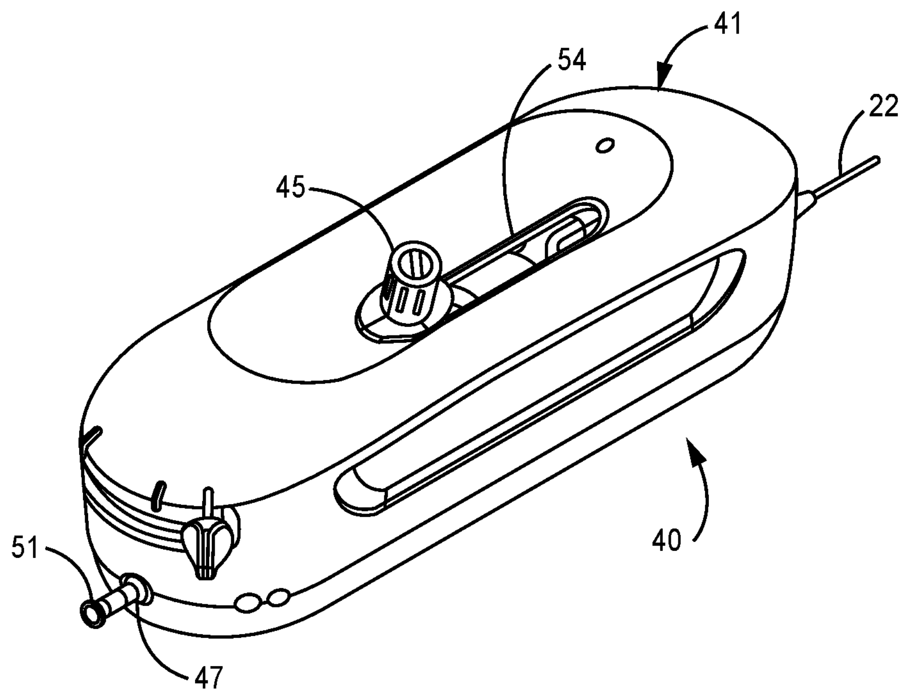
FIG. 5 is a top perspective of a handle of the catheter.
Figure 6:
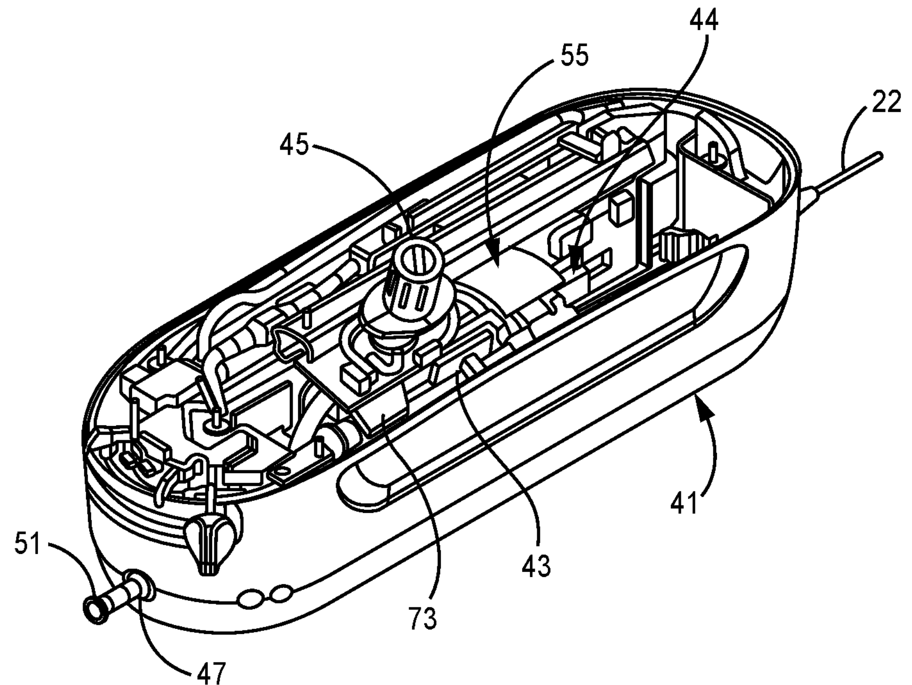
FIG. 6 is a top perspective of the handle with a top housing section removed.
Figure 7:
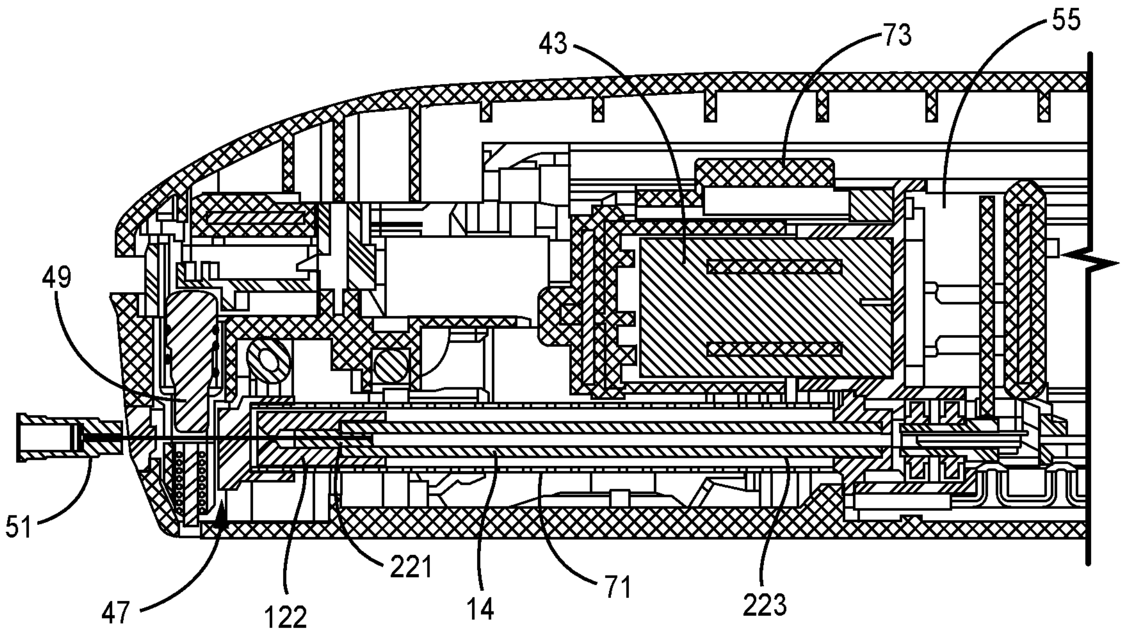
FIG. 7 is a fragmentary longitudinal cross section of the handle.
Figure 8:
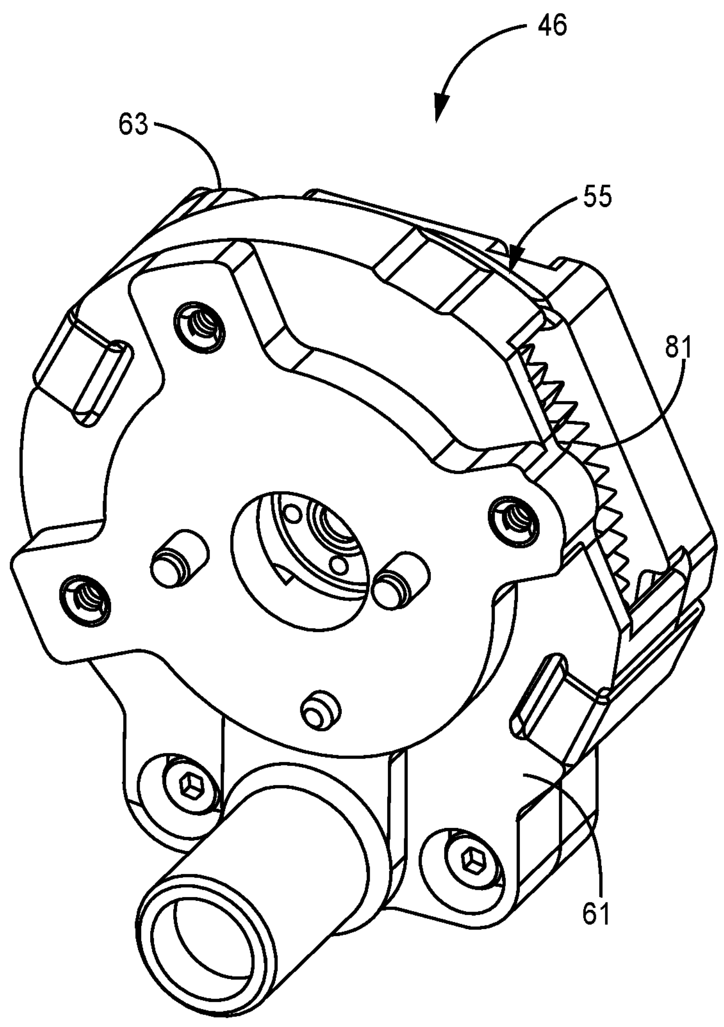
FIG. 8 is a perspective of a gear assembly in the handle.
Figure 9:
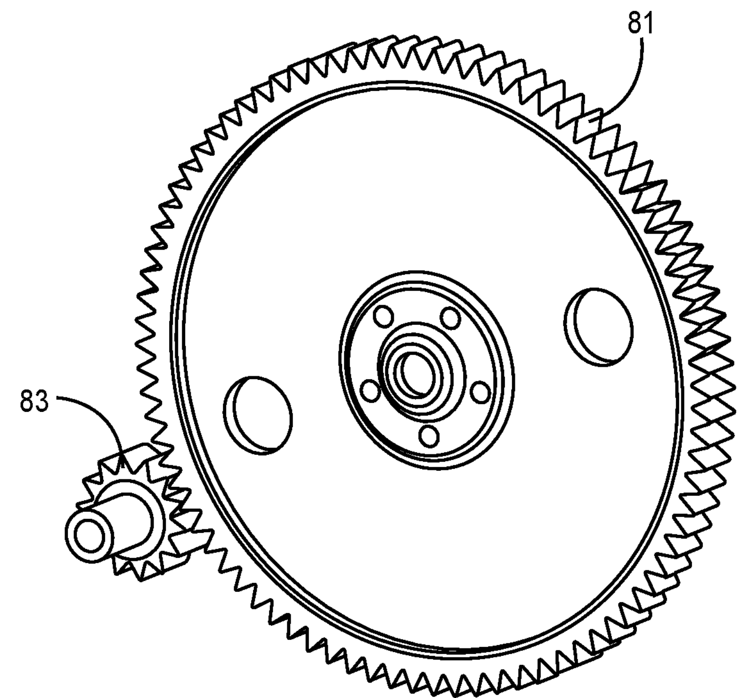
FIG. 9 is a perspective of gears of the gear assembly in the handle.

Referring to FIGS. 1, 5 and 6, the catheter 10 further includes a handle, generally indicated at 40, coupled to a proximal end of the catheter body 11. The handle 40 comprises a housing 41 that supports the components of the handle. As shown in FIGS. 1 and 6, the housing 41 supports an actuator 42 such as a lever (FIG. 6), a button, a dial, a switch, or other devices for selectively actuating a drive, generally indicated at 44, disposed in the handle to drive rotation of the drive coil 12 and burr 20 mounted at the distal end of the drive coil. The drive 44 is configured to rotate the drive coil 12 and burr 20 at speeds of greater than about 80,000 RPM. The drive 44 may be of other types, such as a pneumatic drive, a hydraulic drive, or other types of drives suitable for driving rotation of the drive coil 12. In one embodiment, as shown in FIG. 1, the drive 44 includes a motor 43 (e.g., an electric motor), a gear assembly 46 coupled to the motor, and a drive assembly 48 (e.g., a driveshaft) coupled to the gear assembly and the drive coil 12. In an embodiment, as shown in FIGS. 6-7, the gear assembly 46 includes a gearbox housing 55 that mounts and at least partially encloses a pair of gears for transferring rotation of a shaft of the motor 43 to the drive coil 12. As shown in FIG. 8, the gearbox housing 55 includes a rear housing section 61 and a front housing section 63 formed integrally with the rear housing section such that the gearbox housing comprises a single housing structure. A sleeve portion of the gearbox housing is disposed generally below the rear and front housing sections 61, 63 and attaches to a distal end portion of a guide tube 223. As shown in FIGS. 6-7, the gearbox housing 55 attaches to a carriage or an advancer frame 73 for moving the motor 43 and gear assembly 46 within the housing 41. Further, attaching the gearbox housing 55 to the distal end of the advancer frame 73 secures the motor 43 in the advancer frame so that the motor moves along with the advancer frame. The sleeve portion also receives a portion of drive assembly 48. A driver gear 81 is attached to the motor 43 such that the driver gear rotates with the motor shaft when the motor 43 is activated. As shown in FIG. 9, the driven gear 83 is in mesh with the driver gear 81 so that rotation of the driver gear causes the driven gear to rotate in the opposite direction. The drive assembly 48 attaches the driven gear 83 to the drive coil 12 so that the rotation of the driven gear causes the drive coil to rotate. As shown in FIG. 1, a controller 50 programmed to control operation of the catheter 10 may be provided in the handle 40.

Figure 10:
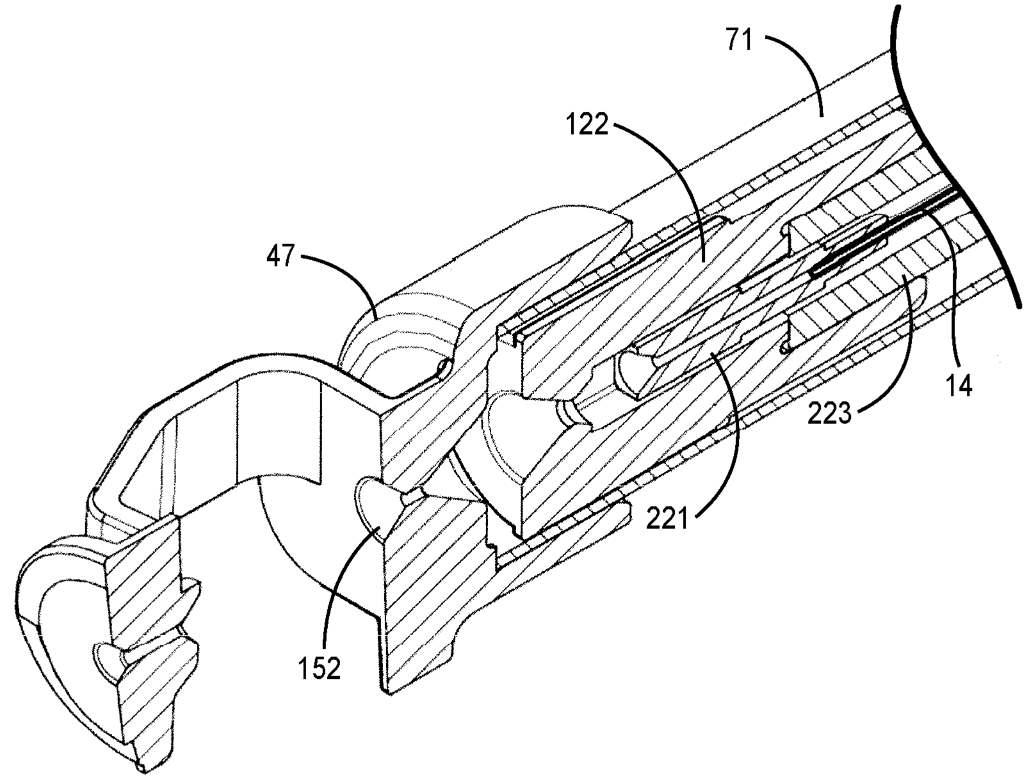
FIG. 10 is an enlarged fragmentary longitudinal cross section of internal components in the handle.
Figure 11:
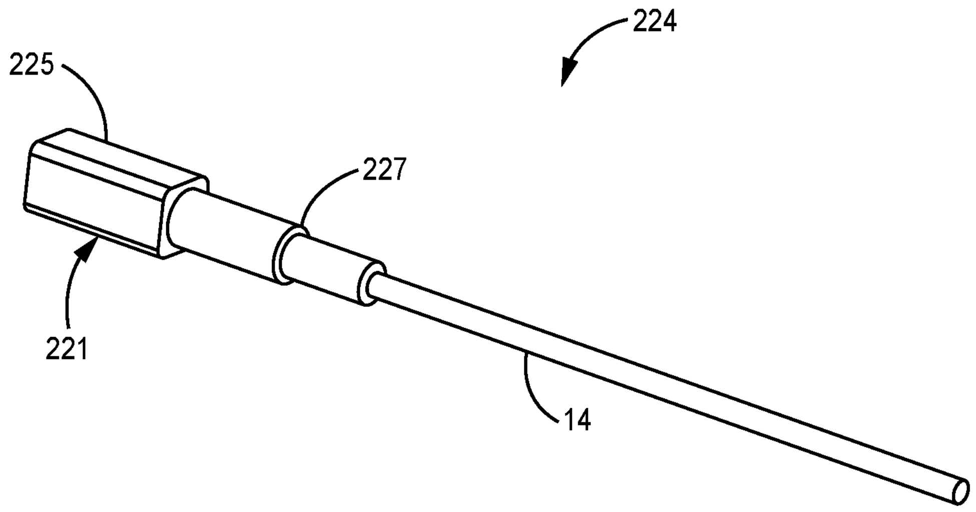
FIG. 11 is a fragmentary perspective of a liner assembly of the catheter.
Figure 12:
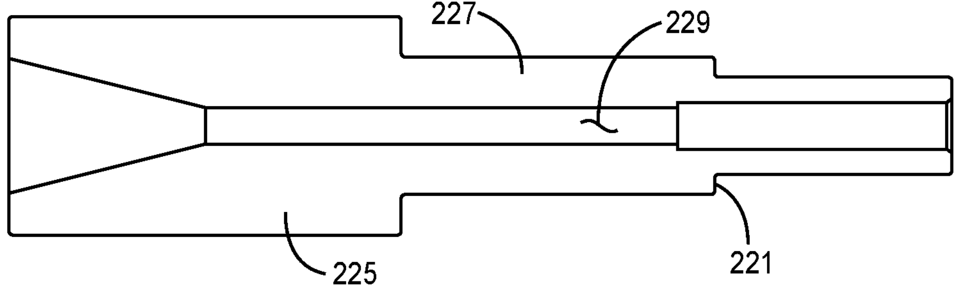
FIG. 12 is a cross section of a liner key of the liner assembly.

Referring to FIGS. 1, 7 and 10, a guidewire port 47 is mounted on a proximal end of a buckle tube 71. The guidewire port 47 provides structure in the handle 40 to support the guidewire 26 at the proximal end of the handle. The guidewire port 47 defines an axial passage 152 (FIG. 10) through which the guidewire 26 extends. Additionally, a guidewire lock 49 (FIG. 7) may be mounted on the guidewire port 47 to lock the guidewire 26 in place relative to the handle. The guidewire lock 49 on the handle 40 may selectively actuated to lock the guidewire 26 relative to the catheter 10 to inhibit linear movement of the catheter on the guidewire while allowing rotation of the drive coil 12 and burr 20 on the guidewire. The guidewire port 47 may also facilitate flushing of the inner liner 14 by passing a cannula 51 through the guidewire port and into the liner key to allow for flushing.

The guide tube 223 extends from the gearbox housing 55 at a distal end of the guide tube to a coupling sleeve 122 at a proximal end of the guide tube. The guide tube 223 is fixedly attached to the gear box housing 55, and the coupling sleeve 122 is fixedly attached to the guide tube 223. In one embodiment, the coupling sleeve 122 is press fit onto an outer surface of the proximal end of the guide tube 223. However, the coupling sleeve 122 can be attached to the guide tube 223 by any suitable means. The coupling sleeve 122 is movably received in the buckle tube 71. The engagement between the coupling sleeve 122 and the buckle tube 71 permits the coupling sleeve and guide tube 223 to translate relative to the buckle tube but prevents rotation of the coupling sleeve and guide tube relative to the buckle tube. In particular, an interior passage in the buckle tube 71 provides sufficient clearance to receive the coupling sleeve 122 for axial movement but does not allow rotational movement of the coupling sleeve in the buckle tube. In one embodiment, axial translation of at least about 70 mm is permitted. It will be understood that the buckle tube 71 and coupling sleeve 122 may be operatively engaged by other means without departing from the scope of the disclosure.

Referring to FIGS. 7 and 10-12, a liner key 221 is attached to a proximal end of the liner 14 and is received in the coupling sleeve 122. As will be discussed in greater detail below, the liner key 221 is configurable to secure the liner key to the coupling sleeve 122. Thus, movement of the coupling sleeve 122 in the buckle tube 71 causes a corresponding movement of the liner key 221 when the liner key is in the coupled configuration. The liner key 221 can also facilitate flushing of the inner liner 14. The liner 14 extends distally from the liner key 221 through the guide tube 223. The liner 14 and liner key 221 may be broadly considered a liner assembly 224. In the illustrated embodiment, the liner key 221 comprises a locking member 225 and an elongate extension member 227 extending distally from a distal end of the locking member. A channel 229 (FIG. 12) extends through the liner key 221. The proximal end of the liner 14 is attached to the extension member 227 to secure the liner to the liner key 221. Thus, the liner key 221 and the liner 14 move together as a single unit. In one embodiment, the liner 14 is received in a portion of the channel 229 extending through the extension member 227. The liner 14 can be retained in the liner key 221 by any suitable means, including without limitation, glue, thermal bond and mechanical bond. In the illustrated embodiment, the locking member 225 comprises a cuboidal structure comprising four flat surfaces. However, the locking member 225 may have other shapes without departing from the scope of the disclosure. In one embodiment, the locking member 225 has a non-circular or non-rounded exterior shape. It is envisioned that the liner key 221, guide tube 223 and buckle tube 71 can have other configurations for permitting relative translation and preventing relative rotation. Further, any suitable materials may be used for the liner key 221, guide tube 223 and buckle tube 71. For example, the liner key 221, can be formed from Peek, Polyoxymethylene (POM), or polycarbonate (PC).

Figure 13A:
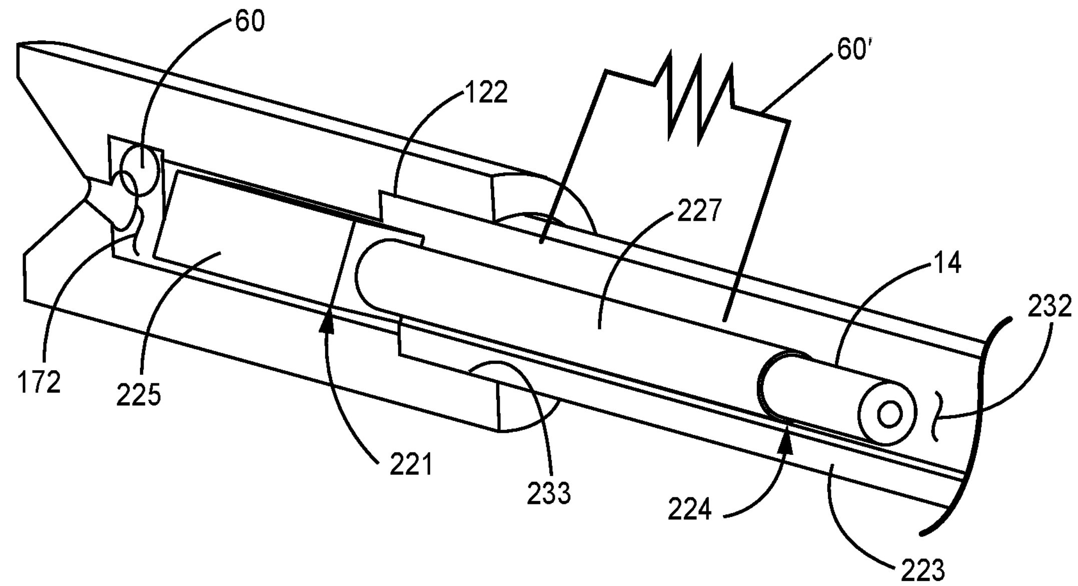
FIG. 13A is a fragmentary longitudinal cross section of the guide tube, coupling sleeve, and liner assembly showing the liner assembly in a first orientation.
Figure 13B:
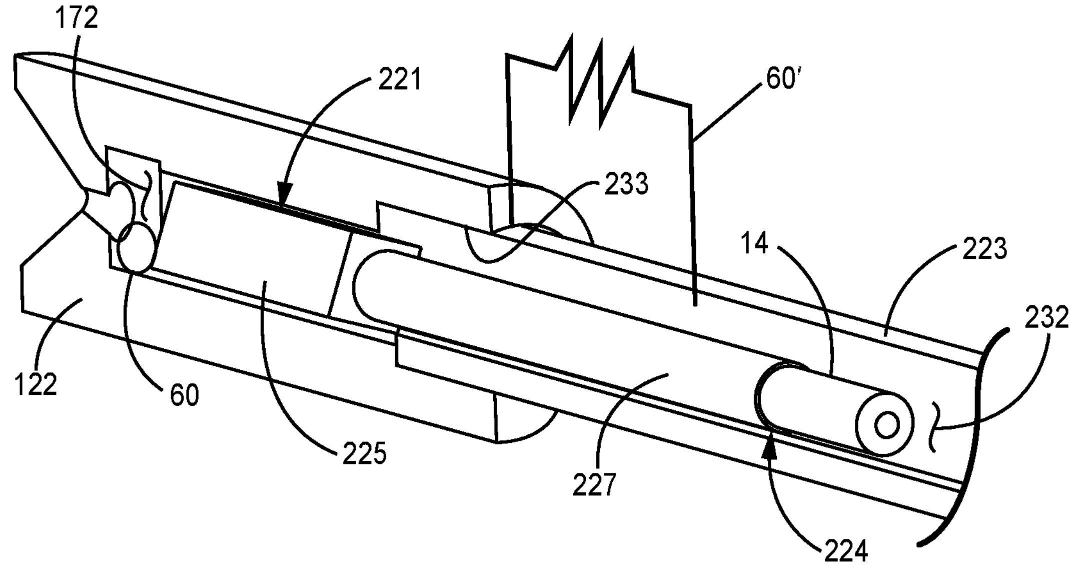
FIG. 13B is a fragmentary longitudinal cross section of the guide tube, coupling sleeve, and liner assembly showing the liner assembly in a second orientation.
Figure 13C:
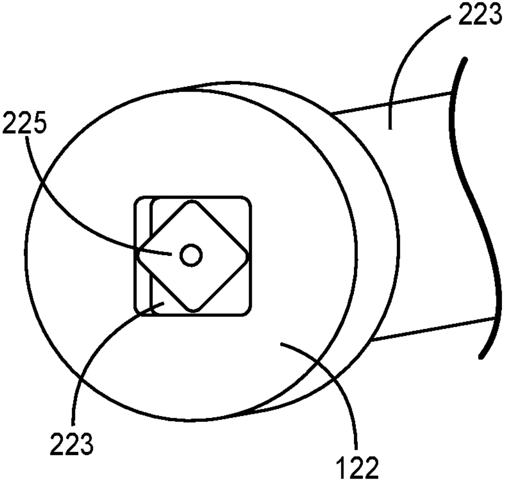
FIG. 13C is fragmentary perspective of the guide tube, coupling sleeve and liner assembly showing the liner assembly in the second orientation.

Referring to FIGS. 13A-13C, to assemble the liner assembly 224 in the catheter 10, the liner assembly is inserted through the guide tube 223 and into a proximal end of the coupling sleeve 122 to secure the liner assembly to the coupling sleeve. In particular, the liner assembly 224 is first inserted through the guide tube 223 where the cuboidal structure of the locking member 225 of the liner key 221 is aligned with a rectangular passage 232 in the guide tube to facilitate insertion of the liner assembly through the guide tube and prevent rotation of the liner key relative to the guide tube. The liner key 221 is then inserted past a proximal opening 233 in the coupling sleeve 122 until a proximal end of the locking member 225 of the liner key is disposed proximally of a proximal-most end of the guide tube 223. As will be explained in greater detail below, the coupling sleeve 122 receives the liner key 221 within the coupling sleeve by sliding engagement in a first orientation, and rotation of the liner key 221 to a second orientation secures the key in the coupling sleeve restricting the key from distal movement out of the coupling sleeve. Therefore, in the illustrated embodiment, the liner key 221 is secured to the coupling sleeve 122 by rotational locking. Further, the coupling sleeve 122 centers the guide tube 223 within the buckle tube 71 which in turn centers and aligns the liner 14 within the drive coil 12. Thus, the liner 14 is prevented from being damaged by the drive coil 12 rotating around the liner. In the illustrated embodiment, the coupling sleeve 122 comprises an elongate member having a generally cylindrical outer surface and an interior passage 172 having a generally rectangular shape defining four planar inner side surfaces. The interior passage 172 is configured to receive the locking member 225 of the key 221 when the liner assembly 224 is inserted into the coupling sleeve 122. In particular, the interior passage 172 receives the locking member 225 when the locking member is in a first rotational orientation whereby the cuboidal structure of the locking member is aligned with the rectangular shape of the interior passage (FIG. 12A). Once the liner key 221 is fully inserted into the coupling sleeve 122 such that an entirety of the locking member 225 is located proximally of the proximal-most end of the guide tube 223, the liner assembly 224 including the liner key 221 can be rotated through a partial rotation causing the locking member 225 to become misaligned with the rectangular passage 172 in the coupling sleeve 122 (FIGS. 13B and 13C). For example, the liner assembly 224 may be rotated between about 30 and about 40 degrees. It is envisioned that other degrees of rotation can be imparted on the liner assembly 224 without departing from the scope of the disclosure. However, it will be understood that the size of the passage 172 limits free rotation of the liner key 221 within coupling sleeve 122. In one embodiment, the liner key 221 engages interior side surfaces of the coupling sleeve 122 to limit free rotation of the key within the coupling sleeve. The misalignment of the locking member 225 with the interior passage 172 causes corners of a distal end of the locking member to come into registration with a proximal end surface of the guide tube 223. Therefore, a distally directed force being exerted on the liner assembly 224 causes the distal end of the locking member 225 to engage the proximal end surface of the guide tube 223 preventing the liner key from being pulled back out of the proximal end of the coupling sleeve 122. Thus, the partial rotation of the liner key 221 locks the liner key in place in the coupling sleeve 122. In the illustrated embodiment, rotation of the liner assembly 224 is caused by rotation of the drive coil 12 by the motor 43. Accordingly, the liner assembly 224 has a first orientation prior to rotation of the drive coil 12 to rotate the tissue-removing element 20 and a second orientation after rotation of the elongate body. It will be understood that the coupling sleeve 122 could have other shapes without departing from the scope of the disclosure. For example, broadly, the coupling sleeve 122 may have a non-circular or non-rounded exterior shape. The coupling sleeve 122, guide tube 223, gearbox housing 55 and advancer frame 73 may be broadly considered a coupling assembly for coupling the liner assembly 224, including the inner liner 14, to an advancer 45.

Figure 14:
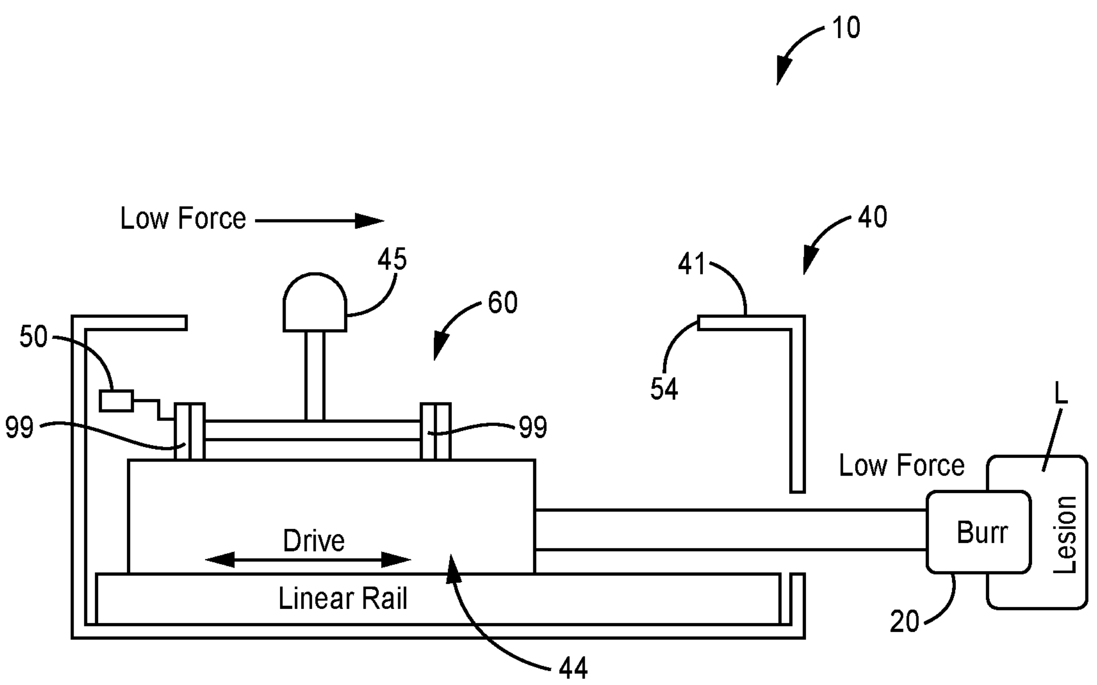
FIG. 14 is a schematic illustration of another embodiment of the catheter showing a linear force applied to an advancer, a force indicator includes at least one load cell.
Figure 15:
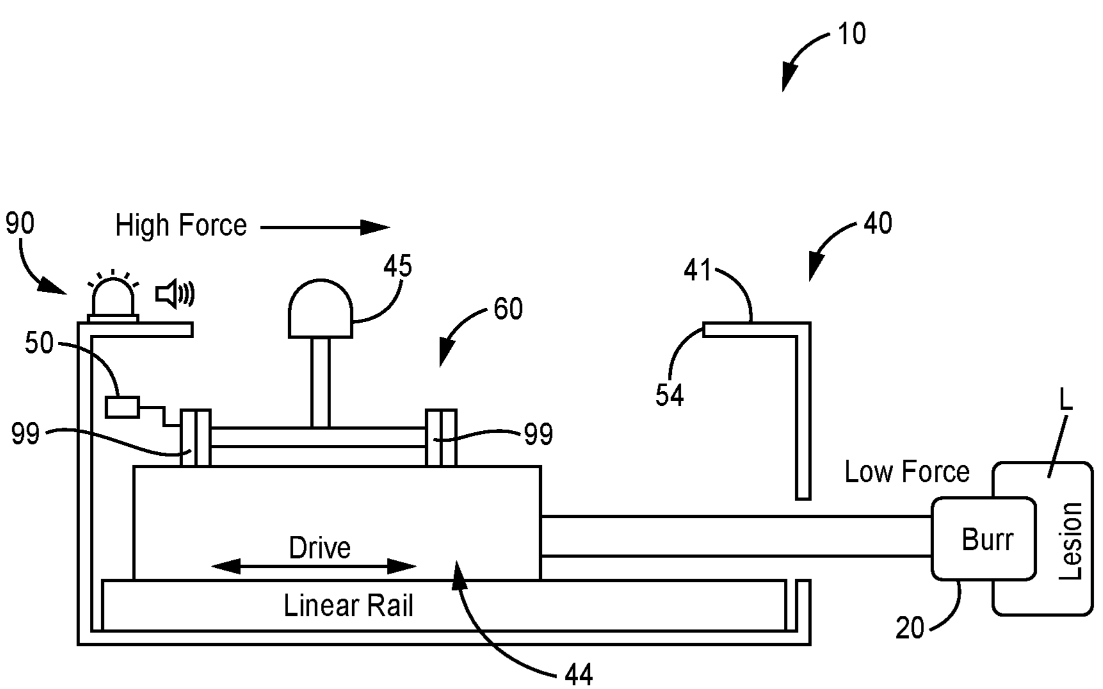
FIG. 15 is similar to FIG. 14 showing a high linear force applied to the advancer.

Referring to FIGS. 1, 14 and 15, the advancer 45 (e.g., a slide) of the handle 40 is operatively coupled to the drive 44 to selectively translate (e.g., linearly advance) the drive together with the drive coil 12 and the burr 20 to advance and retract the drive coil and burr relative to the handle and the isolation sheath 22 at the distal end of the sheath. The drive 44 may be coupled to a linear rail or other track or guide. The housing 41 of the handle 40 may define a slot 54 which limits the movement of the advancer 45 relative to the handle. Thus, the length of the slot 54 determines the amount the burr 20 may be linearly advanced or displaced from the distal end of the isolation sheath 22 during tissue removal operation. In one embodiment, the slot 54 has a length of about 70 mm (2.8 inches), and thus the burr may be selectively advanced 70 mm (2.8 inches) between a fully retracted, proximal position to a fully advanced, distal position relative to the isolation sheath 22.

Figure 19:
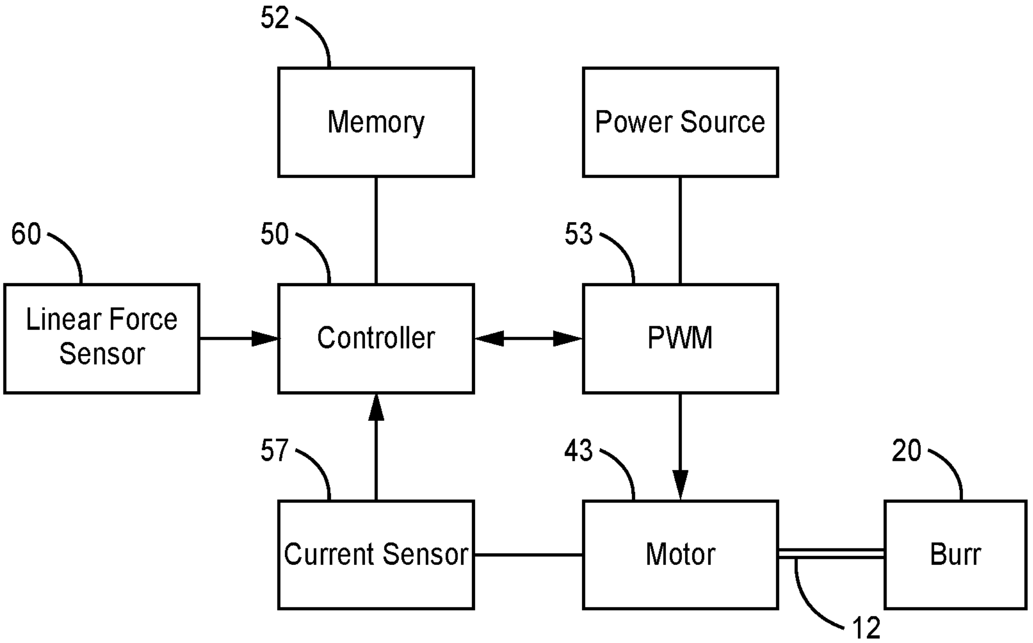
FIG. 19 is a system representation of the catheter.

Referring to FIG. 19, during rotation of the drive coil 12 by the motor 43, torque is transferred from the motor to the drive coil. The motor 43 may be powered by a battery (external or internal) or other internal or external electrical power source. When power (e.g., voltage) is applied to the motor 43 from the power source, the electrical energy is converted into mechanical energy to rotate the drive assembly 48 for rotating the drive coil 12 and the burr 20. Further, the speed of the motor 43 may be controlled by adjusting voltage applied to the motor, such as through pulse width modulation (PWM) of the voltage. Therefore, through the use of PWM, the speed of the motor 43 can be adjusted, as will be explained in greater detail below. The controller 50 or another controller (e.g., a PWM controller 53) may be configured to control voltage through PWM. As explained in more detail below, the controller 50 (or another controller) is configured to monitor torque in the system (e.g., torque at the motor, torque at the drive coil, and/or torque at the burr). For example, the current being drawn by the motor may be monitored by the controller 50 or another controller. For example, a motor current sensor 57 may be in communication with the controller 50 and used as an input for the controller operating the voltage supplied to the motor 43. This detected current may be used in monitoring torque, and thus, the current sensor functions as a torque sensor indicative of torque in the system. Torque in the system may be determined in other ways, including but not limited to a load sensor or other directing sensing of torque, rather than monitoring current.

In addition to torque, the catheter 10 is configured to determine and monitor linear force in the system (e.g., linear force applied to the lesion by the rotating burr). In one example, referring back to FIG. 19, the catheter 10 includes a linear force sensor 60, which indicates the amount of linear force in the system. One example of an implementation of the linear force sensor is shown in FIGS. 14 and 15. During ablation and as the burr 20 is being rotated by the drive 44, the user applies force to the advancer 45 to move the rotating burr against the obstruction L (e.g., lesion) in the lumen. The obstruction L in turn, applies a counterforce back to the burr, which is transferred along the catheter to the advancer 45. Thus, the linear force applied at the advancer 45 is indicative of the amount of linear force applied to the lesion by the burr 20. In this embodiment, the force sensor 60 may include one or more load cells 99 (e.g., button load cells) configured to sense or detect force applied to the advancer 45. The load cells 99 are coupled to the drive 44 and the advancer 45, e.g., arms of the advancer, engage the load cells. Electrical signals generated by the load cells 99 may be used by the controller 50 to determine the amount of linear force being applied to the advancer 45, which is in turn indicative of linear force load at the burr.

Linear force may be detected and/or monitored in other ways. For example, rather than using the force applied to the drive 44 by the advancer, the linear force being applied at the proximal end of the inner liner 14 may be detected and monitored. For example, as shown in FIGS. 13A and 13B, the sensor 60 may be located proximal to the liner key 221 such that force from the liner key on the sensor may be used to calculate the linear force in the system. In this example, a back-face of the liner key 221 may remain independent from the sensor such that a change in resistance of the back-face is used to measure force. Through this arrangement, the linear force being exerted on the liner 14 is used as the linear force reference for the system. Additionally, or alternatively, as shown in FIGS. 13A and 13B, a sensor 60' may be coupled to another portion of the catheter body 11, such as the coupling sleeve 122, and the inner liner 14 such that force on the sensor may be used to calculate the linear force in the system. For example, but not limiting to, the sensor 60' may be a resistive sensor.

As shown in FIG. 15, the catheter may also include an alarm 90 configured to be activated by the controller 50, as explained below. The alarm 90 may be one or more of an auditory alarm (e.g., a buzzer or beeper), a visual alarm (e.g., a light, or a flashing light, such as an LED), or a haptic alarm (e.g., vibration). The alarm 90 may be coupled to the handle.

Speed Control of Motor Based on Torque and Linear Force

In the present disclosure, during ablation as the tissue-removing element is rotating and engaging the lesion L for ablation (e.g., during an ablation mode), the monitored torque in the system (e.g., estimated torque at the drive assembly or at the burr) and the monitored linear force in the system (e.g., estimated linear force at the burr) are used as inputs for a motor control operation by the controller.

In one example, during ablation the estimated torque at the rotating burr 20 is monitored by monitoring the current being drawn by the motor 43, and the input voltage (e.g., modulated voltage). In other words, the controller 50 may be configured (i.e., programmed) to use the input voltage and the instantaneous current being drawn by the motor to determine (e.g., estimate) torque in the system. A calibration process may be used for programming the controller 50. The calibration process calculates the mechanical torque delivered to the catheter 10 as a quadratic function of motor voltage and motor current. The catheter speed is also calculated as a quadratic function of motor voltage and the measured torque load in the system. The calibration process is initiated by measuring motor current and speed values in response to a series of motor drive PWM torque load combinations. In particular, speed contributions of the catheter 10 are modeled using a quadratic transfer function for the change in speed as a function of motor drive PWM and torque load. The transfer functions assume the catheter 10 is in compression since the in use conditions of the catheter primarily place the catheter in compression and the overestimation of torque in the compression state provides an over-torqueing buffer built into the calibration.

In one embodiment, the controller 50 is configured to select a torque response routine, from a plurality of torque response routines. Selection of the torque response routine by the controller 50 is based on the monitored linear force. For each torque response routine, the controller 50 may be programmed to control operation of the motor 43 in response, at least in part, to the estimated torque in the system (e.g., the drive assembly 48). For example, the controller 50 may implement a torque response routine during ablation where the motor drive PWM duty cycle is set using a 2-dimensional lookup table based on motor current measurements and input PWM duty cycle values to output new PWM duty cycles, which in turn control the speed of the motor 43. In one embodiment, the catheter 10 implements a two-factor lookup procedure whereby the controller 50 monitors the motor current and existing PWM values to new motor drive PWM duty cycle values to estimate the torque in the system. The procedure provides a direct correlation between motor drive PWM and motor current with an estimated torque in the system. The lookup table may be stored in the catheter memory 52 at manufacturing which provides estimated torque values for a given motor current value and motor drive PWM value pair. In particular, the lookup table is populated with motor drive PWM values and motor current values which correspond to an estimated torque value. Using this lookup table, the torque control routine can be performed quickly by the controller 50.

Figure 16:
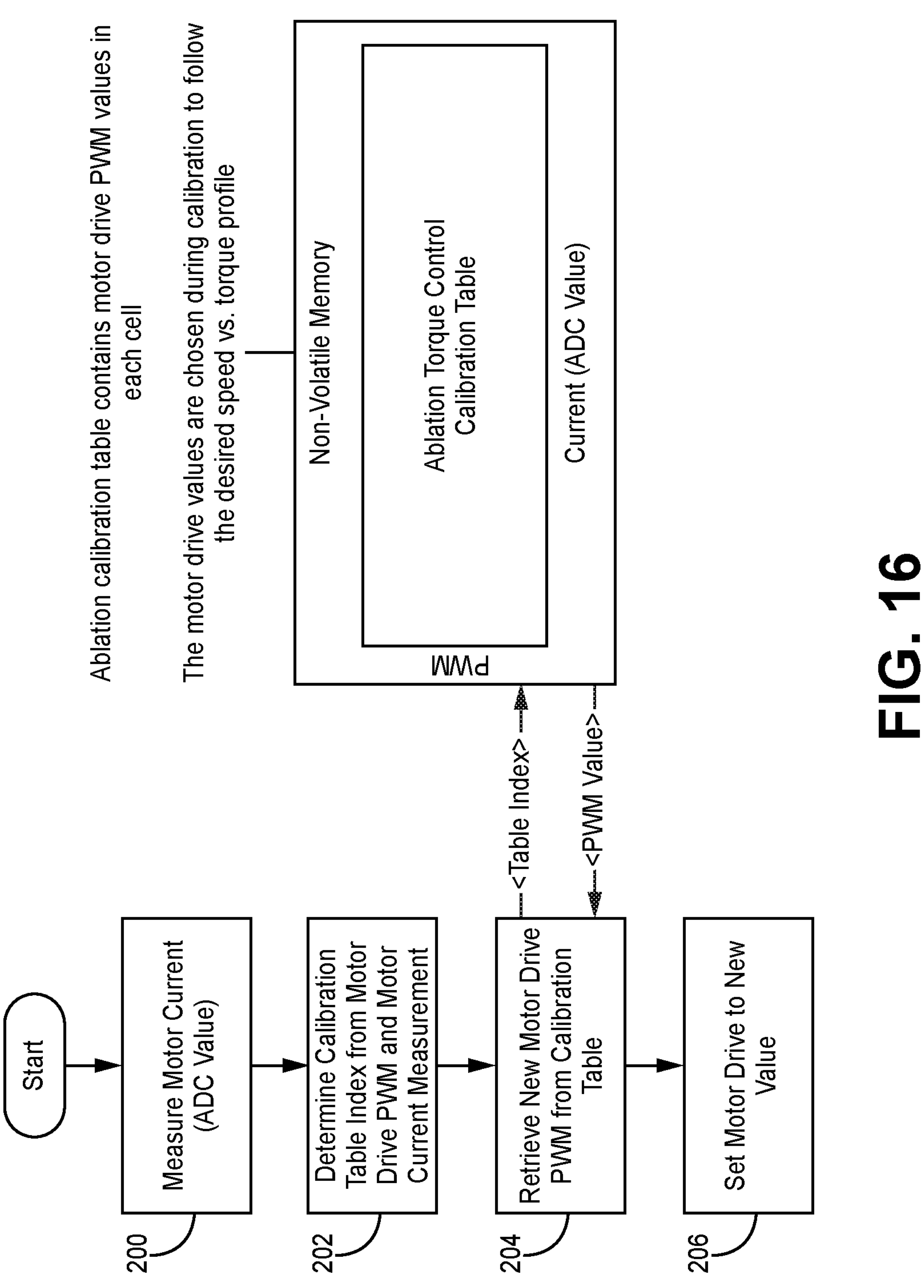
FIG. 16 is a flow chart of a torque control routine of the catheter.

Referring to FIG. 16, an example of a torque response routine or algorithm is shown. At 200, the motor current is sampled to receive an ADC value. The current motor drive PWM is also known at the time of sampling. Then at 202, a calibration table index is determined from the motor drive PWM and motor current measurements. From the calibration table index, a new motor drive PWM value is selected by referencing the lookup table at 204. The lookup table provides a new motor drive value that corresponds to the measured motor current and input PWM value, and the new PWM value is applied at 206.

Figure 17:
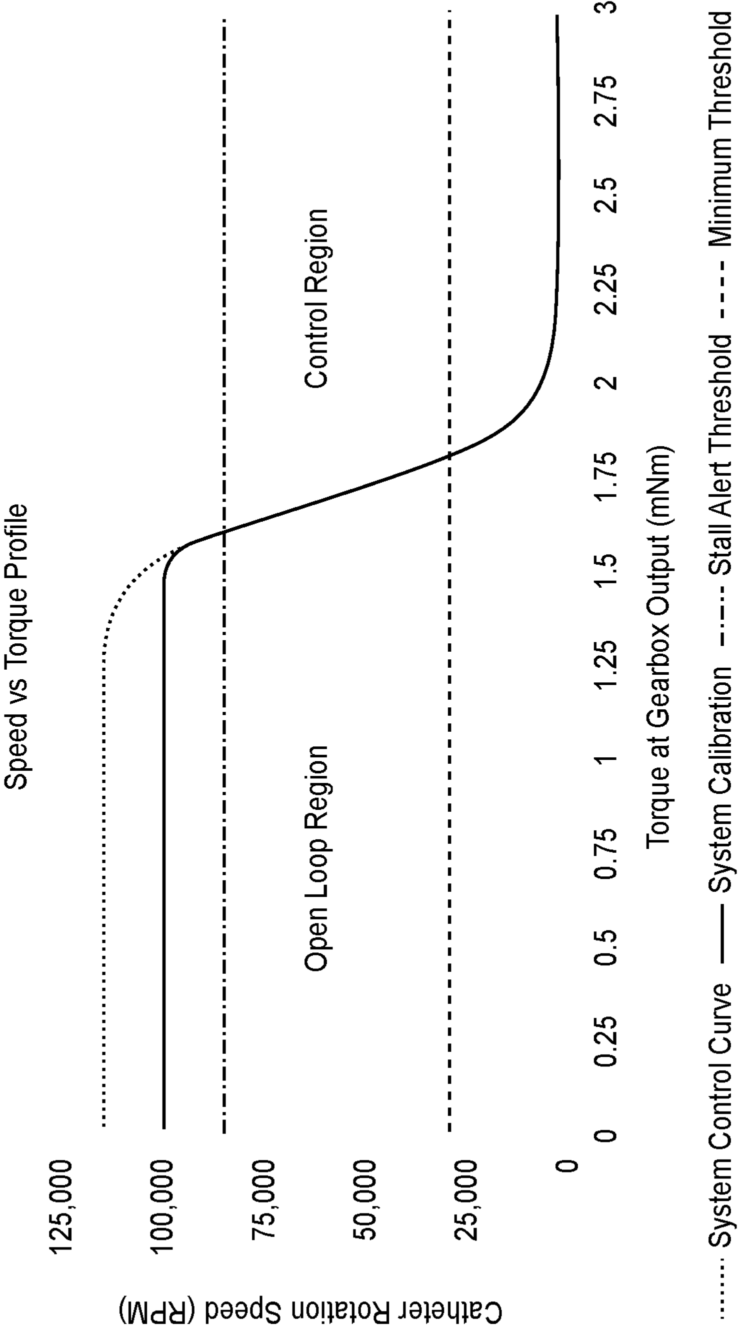
FIG. 17 is a graph of a speed control profile used by the catheter.

The PWM values populated in the lookup table correspond to a desired speed along a control profile. As shown in FIG. 17, a speed control curve may comprise a logistic curve that determines the desired speed for a given torque load. In one embodiment, the logistic curve may be as follows:

$$RPM = \left(\Theta_1 + \frac{\Theta_2 - \Theta_1}{1 + e^{\left(\frac{T-\Theta_3}{\Theta_4}\right)}}\right)(1000)$$

where T is the estimated torque at the drive assembly 48 and the four Θ coefficients are predetermined calibration values. In one embodiment, $\theta_1$, =−3 (low speed), $\theta_2$,=115 (calculated speed for 0.5 mNm (high speed)), $\theta_3$,=1.7 (torque for mid-point speed), and $\theta_4$,=0.09 (torque curve mid ramp). Thus, a desired motor speed (RPM) can be calculated from the estimated torque load in the system.

In the present embodiment, the torque response routines differ from one another by the value of one or more of the above coefficients. These coefficients are selected during calibration so that the desired speed response is based on both the estimated torque and the linear force in the system. Thus, it is envisioned that the torque response routines will have look-up tables having different new motor drive values that correspond to the measured motor current and input PWM value. In this way, the catheter is configured to use linear force as an additional input or parameter for controlling speed based on torque.

Figure 18:
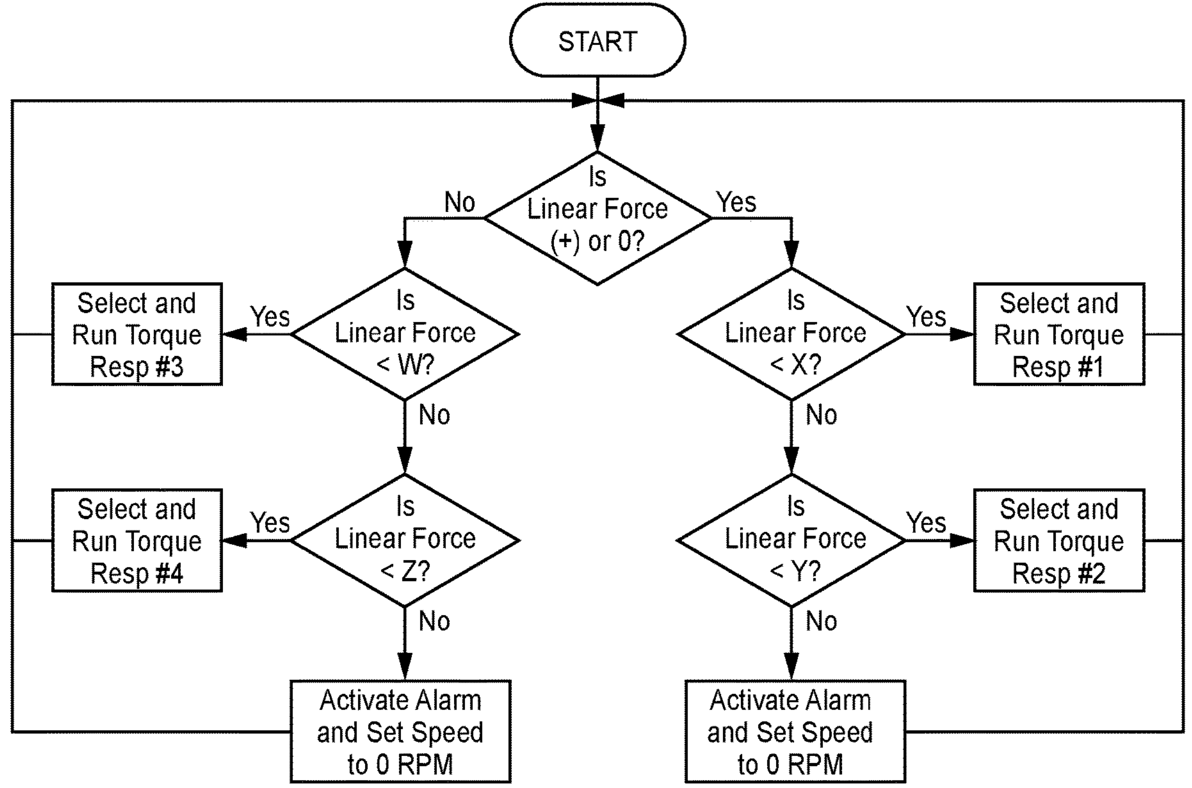
FIG. 18 is a flow chart representing an algorithm for determining torque control routine.

An example of a suitable algorithm for using linear force as a parameter in controlling speed is represented in FIG. 18. In general, this algorithm is a stepwise function where the controller 50 selects a torque response routine to run based on where the detected linear force falls within predetermined ranges of forces. As explained above, each of the torque response routines may have different speed control curves tuned to specific conditions. For example, a change in speed response may be through changing at least one of the Θ coefficients, which changes the speed control curve.

Referring still to FIG. 18, in this example when the monitored linear force is between from 0 N to +X N, the controller 50 is configured to select a first torque response routine and apply the first torque response routine to control speed of the motor based on monitored torque. (The positive sign "+" signifies that the burr is applying the linear force in the distal or forward direction. Similarly, a negative sign "–" signifies that the burr is applying the linear force in the proximal or rearward direction. Thus, in this example, "+X N" represents a vector having a magnitude of X in the distal direction). In this same example, when the monitored linear force is great than +X N and less than +Y N, the controller 50 is configured to select a second torque response routine and apply the second torque response routine to control speed of the motor 43 based on monitored torque. If the monitored force is greater than +Y N, the controller 50 may be configured to activate the alarm 90 and reduce the speed to 0 RPM. It is understood that there may be any number of force ranges between 0 N and the threshold force (e.g., +Y N) at which the controller 50 is configured to activate the alarm 90 and reduce the speed to 0 RPM. In this example, a similar logic is executed by the controller 50 for linear force applied in the proximal or rearward direction. When the monitored linear force is between from 0 N to −W N, the controller 50 is configured to select a third torque response routine and apply the third torque response routine to control speed of the motor 43 based on monitored torque. In this same example, when the monitored linear force is great than-W N and less than −Z N, the controller 50 is configured to select a fourth torque response routine and apply the fourth torque response routine to control speed of the motor 43 based on monitored torque. If the monitored force is greater than −Z N, the controller 50 may be configured to activate the alarm 90 and reduce the speed to 0 RPM. It is understood that there may be any number of force ranges between 0 N and the threshold force (e.g., −Z N) at which the controller 50 is configured to activate the alarm 90 and reduce the speed to 0 RPM. This process is repeated at a preset time interval to continuously control the motor 43 during ablation. In one embodiment, the process is repeated every 25 microseconds (40 kHz). It will be understood that the process could be repeated at other time intervals without departing from the scope of the disclosure.

In another example, a torque response routine may be dynamic, with the coefficients (i.e., parameters) of the logistic curve varying continuously as a function of the monitored linear force. The coefficients of the response function can themselves be a function of the applied force, allowing modification of the torque response in a continuous manner. One system for establishing such equations would be to establish response at set points within the predetermined threshold ranges and fit an appropriate regression curve to the set points, allowing for continuous change over the predetermined threshold ranges. In this example, parameters $\theta_1$, $\theta_2$, $\theta_3$ and $\theta_4$ may be replaced with functions of $\theta_1$ (F), $\theta_2$ (F), $\theta_3$ (F), and/or $\theta_4$ (F), such as follows:

$$RPM = (\Theta_1 + \frac{\Theta_2(F) - \Theta_1(F)}{1 + e^{\left(\frac{T - \Theta_3(F)}{\Theta_4(F)}\right)}})(1000)$$

In one embodiment, the speed control may include an adaptive profile subject to users and type of use (e.g., forward versus reverse ablation) to modify for different users and ablation strategies, allowing for different speed responses. For example, the system may include more than one modes selectable by the user. Each of the modes has a different speed control operation.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue in a body lumen, the tissue-removing catheter comprising:

an elongate body having an axis and proximal and distal end portions spaced apart from one another along the axis, the elongate body being sized and shaped to be received in the body lumen;

a motor operatively coupled to the elongate body for imparting torque to the elongate body to drive rotation of the elongate body;

a tissue-removing element mounted on the distal end portion of the elongate body and configured to rotate with the elongate body, the tissue-removing element being configured to remove the tissue as the tissue-removing element is rotated by the elongate body within the body lumen;

an advancer operatively coupled to the motor to selectively apply a linear force to the motor together with the elongate body and the tissue-removing element to linearly advance and retract the motor, the elongate body and the tissue-removing element;

a torque sensor configured to sense torque from the motor acting on a component of the catheter;

a linear force sensor configured to sense a linear force from the advancer acting on a component of the catheter;

a controller in operative communication with the motor, the torque sensor, and the linear force sensor, wherein the controller is configured to control a speed of the motor based on the sensed torque and the sensed linear force during operation of the tissue-removing catheter, and wherein the controller is further configured to select and run a torque response routine from a plurality of torque response routines of different speed control curves tuned to specific conditions.

2. The tissue-removing catheter of claim 1, wherein the torque sensor is configured to sense current being drawn by the motor to determine output torque of the motor.

3. The tissue-removing catheter of claim 2, wherein the controller is configured to control a voltage applied to the motor to control the speed of the motor based on the sensed torque and the sensed linear force during operation of the tissue-removing catheter.

4. The tissue-removing catheter of claim 3, wherein the voltage is a pulse-width modulated voltage.

5. The tissue-removing catheter of claim 4, wherein selection of the torque response routine by the controller is based on the sensed torque, the sensed linear force, and a pulse-width modulated voltage value inputted to the motor during operation of the tissue-removing catheter.

6. The tissue-removing catheter of claim 5, further comprising computer-readable memory in communication with the controller, wherein a lookup table is stored in the computer-readable memory, the look-up table including the plurality of torque response routines.

7. The tissue-removing catheter of claim 6, wherein the look-up table includes a plurality of look-up tables, each look-up table is a 2-factor look-up table associated with a range of linear force values, each 2-factor look-up table including a plurality of pulse-width modulated voltage value/motor current pairs corresponding to a desired pulse-width modulated voltage value, the controller referencing the 2-factor lookup table to select and apply a determined pulse-width modulated voltage value to the motor.

8. The tissue-removing catheter of claim 2, wherein the controller is configured to control the speed of the motor based further on voltage inputted to the motor.

9. The tissue-removing catheter of claim 1, wherein selection of the torque response routine by the controller is based in part on the linear force sensed by the linear force sensor.

10. The tissue-removing catheter of claim 9, wherein the controller is configured to determine a range, from a plurality of ranges of linear force values, within which the sensed linear force falls, the controller configured to select and run a torque response routine to control speed of the motor based on the determined range of linear force values in which the sensed linear force falls.

11. The tissue-removing catheter of claim 1, wherein the elongate body comprises a drive shaft, the tissue-removing catheter further comprising a liner extend along the axis of the drive shaft and configured to receive a guidewire therein, the linear force sensor being operatively coupled to the liner to sense a linear force from the advancer acting on the liner.

12. A method of using the tissue-removing catheter of claim 1, the method comprising:
- sensing torque by the torque sensor by monitoring torque drawn by the motor;
- sensing linear force from the advancer acting on the component of the catheter;
- selecting the torque response routine based on the sensed linear force and the sensed torque; and
- applying the selected torque response routine to control the speed of the motor.

13. A tissue-removing catheter for removing tissue in a body lumen, the tissue-removing catheter comprising:
- a drive shaft having an axis and proximal and distal end portions spaced apart from one another along the axis, the drive shaft being sized and shaped to be received in the body lumen;
- a liner received in the elongate drive shaft, the liner configured to receive a guidewire therein;
- a motor operatively coupled to the drive shaft for imparting torque to the drive shaft to drive rotation of the drive shaft;
- a tissue-removing element mounted on the distal end portion of the drive shaft and configured to rotate with the drive shaft, the tissue-removing element being configured to remove the tissue as the tissue-removing element is rotated by the drive shaft within the body lumen;
- an advancer operatively coupled to the motor to selectively apply a linear force to the motor together with the drive shaft and the liner to linearly advance and retract the drive shaft, the liner, and the tissue-removing element; and
- a linear force sensor configured to sense a linear force indicative of linear force that is imparted by the advancer, wherein the linear force sensed by the linear force sensor is a linear force imparted on the liner.

14. The tissue-removing catheter of claim 13, wherein the linear force sensor is operatively coupled to the liner to sense the linear force from the advancer acting on the liner.

15. The tissue-removing catheter of claim 14, wherein the linear force sensor measures change in resistance between the liner and another portion of the elongate body.

16. The tissue-removing catheter of claim 13, further comprising a controller in operative communication with the motor and the linear force sensor, wherein the controller is configured to control a speed of the motor based on the sensed linear force during operation of the tissue-removing catheter.

17. The tissue-removing catheter of claim 16, further comprising a torque sensor configured to sense torque from the motor acting on a component of the catheter, wherein the controller is in operative communication with the torque sensor, wherein the controller is configured to control the speed of the motor based on the sensed torque and the sensed linear force during operation of the tissue-removing catheter.

18. A tissue-removing catheter for removing tissue in a body lumen, the tissue-removing catheter comprising:
- an elongate body having an axis and proximal and distal end portions spaced apart from one another along the axis, the elongate body being sized and shaped to be received in the body lumen;
- a motor operatively coupled to the elongate body for imparting torque to the elongate body to drive rotation of the elongate body;
- a tissue-removing element mounted on the distal end portion of the elongate body and configured to rotate with the elongate body, the tissue-removing element being configured to remove the tissue as the tissue-removing element is rotated by the elongate body within the body lumen;
- an advancer operatively coupled to the motor to selectively apply a linear force to the motor together with the elongate body and the tissue-removing element to linearly advance and retract the motor, the elongate body and the tissue-removing element;
- a torque sensor configured to sense torque from the motor acting on a component of the catheter;
- a linear force sensor configured to sense a linear force from the advancer acting on a component of the catheter;
- a controller in operative communication with the motor, the torque sensor, and the linear force sensor, wherein the controller is configured to control a speed of the motor based on the sensed torque and the sensed linear force during operation of the tissue-removing catheter;
- wherein the controller is configured to calculate and run a torque response routine to control the speed of the motor, wherein the calculated torque response routine is a function of the sensed torque and at least one parameter, wherein the at least one parameter is a function of the sensed linear force, and wherein the torque response routine comprises a logistic curve.

* * * * *